(12) United States Patent
Schnier et al.

(10) Patent No.: US 10,013,771 B2
(45) Date of Patent: Jul. 3, 2018

(54) DEVICE AND METHOD FOR OPTICAL QUALITY CONTROL OF THE COATING OR STAINING OF A KERNEL-TYPE SUBSTRATE

(71) Applicant: BAYER CROPSCIENCE AG, Monheim (DE)

(72) Inventors: Heinz-Friedrich Schnier, Leverkusen (DE); Franco Fois, Monheim (DE)

(73) Assignee: BAYER CROPSCIENCE AG, Monheim (DE)

( * ) Notice: Subject to any disclaimer, the term of this patent is extended or adjusted under 35 U.S.C. 154(b) by 103 days.

(21) Appl. No.: 14/407,099

(22) PCT Filed: Jun. 7, 2013

(86) PCT No.: PCT/EP2013/061853
§ 371 (c)(1),
(2) Date: Dec. 11, 2014

(87) PCT Pub. No.: WO2013/186144
PCT Pub. Date: Dec. 19, 2013

(65) Prior Publication Data
US 2015/0178948 A1    Jun. 25, 2015

(30) Foreign Application Priority Data

Jun. 13, 2012  (EP) .................................... 12171733

(51) Int. Cl.
*G06K 9/00*  (2006.01)
*G06T 7/40*  (2017.01)
(Continued)

(52) U.S. Cl.
CPC .......... *G06T 7/408* (2013.01); *A01D 41/1277* (2013.01); *G01N 21/8422* (2013.01); *G01N 21/85* (2013.01); *G01N 21/8806* (2013.01); *G06T 7/40* (2013.01); *G06T 7/90* (2017.01); *G01N 2021/8427* (2013.01);
(Continued)

(58) Field of Classification Search
None
See application file for complete search history.

(56) References Cited

U.S. PATENT DOCUMENTS 5,321,764 A * 6/1994 Cullen ............... G01N 15/1468
209/576
5,761,540 A * 6/1998 White ................ G01N 21/8806
362/16
(Continued)

FOREIGN PATENT DOCUMENTS

| WO | 2006010761 A1 | 2/2006 |
| WO | 2007068056 A1 | 6/2007 |
| WO | 2009045035 A1 | 4/2009 |

OTHER PUBLICATIONS

International Search Report from corresponding PCT/EP2013/061853, dated Oct. 1, 2013.

*Primary Examiner* — Matthew Bella
*Assistant Examiner* — Jose M Torres
(74) *Attorney, Agent, or Firm* — McBee Moore Woodward & Vanik IP, LLC

(57) ABSTRACT

The invention relates to a device and a method for optical quality control of the coating or staining of a kernel-type substrate, in particular seed with a color and contrast intensive coating composition.

6 Claims, 9 Drawing Sheets

(51) Int. Cl.
*A01D 41/127* (2006.01)
*G01N 21/85* (2006.01)
*G01N 21/84* (2006.01)
*G01N 21/88* (2006.01)
*G06T 7/90* (2017.01)

(52) U.S. Cl.
CPC . *G01N 2021/8466* (2013.01); *G06K 2209/17* (2013.01); *G06T 2207/10024* (2013.01)

(56) References Cited

U.S. PATENT DOCUMENTS

| | | | | |
|---|---|---|---|---|
| 5,835,206 A * | 11/1998 | Tragesser | ............ | G01N 21/25 356/406 |
| 6,646,264 B1 * | 11/2003 | Modiano | ............ | G01N 21/359 250/339.07 |
| 7,119,930 B1 * | 10/2006 | Carstensen | ............ | H04N 5/2256 250/201.3 |
| 7,218,775 B2 * | 5/2007 | Kokko | ............ | G06K 9/00127 382/155 |
| 8,605,149 B2 * | 12/2013 | Conrad | ............ | G06K 9/00 348/135 |
| 2001/0012389 A1 * | 8/2001 | Welchman | ............ | G01N 21/951 382/141 |
| 2004/0141641 A1 * | 7/2004 | McDonald, Jr. | ... | G06K 9/00127 382/159 |
| 2005/0074146 A1 | 4/2005 | Jones et al. | | |
| 2008/0310674 A1 * | 12/2008 | Modiano | ............ | B07C 5/34 382/100 |
| 2009/0046890 A1 * | 2/2009 | Hausmann | ............ | G06T 7/0012 382/100 |
| 2010/0208936 A1 * | 8/2010 | Beaty | ............ | G06T 7/20 382/100 |
| 2011/0150289 A1 * | 6/2011 | Ringenbach | ............ | G06T 7/0004 382/110 |
| 2012/0165973 A1 * | 6/2012 | Earlam | ............ | B07C 5/00 700/223 |

\* cited by examiner

Section A-A

Section B-B

DEVICE AND METHOD FOR OPTICAL QUALITY CONTROL OF THE COATING OR STAINING OF A KERNEL-TYPE SUBSTRATE

CROSS REFERENCE TO RELATED APPLICATIONS

This application is a § 371 National Stage Application of PCT/EP2013/061853, filed Jun. 7, 2013, which claims priority to EP 12171733.4, filed Jun. 13, 2012.

BACKGROUND

Field of the Invention

The invention relates to a device and a method for optical quality control of the coating or staining of a kernel-type substrate, in particular seed with a colour and contrast intensive coating composition.

Description of Related Art

In addition to the applied amount of the treatment composition (treatment level), the homogeneous distribution of the applied treatment composition, the so called kernel-to-kernel distribution, is also a substantial quality factor in the case of seed treatment. In turn, a distinction should be made here between:
- the distribution of the treatment composition on the individual kernel,
- the distribution of the treatment composition between the kernels (kernel-to-kernel distribution).

In the prior art, the treatment composition is distributed between the kernels by wet chemical extraction and quantitative measurement (e.g. by means of HPLC).

In the prior art, the distribution of the treatment composition on the individual kernel is established by means of optical detection via colour measurement (e.g. yellow grain—red treatment composition) on individual kernels of an extracted sample.

Accordingly, the quality control is a complicated process which keeps an analysis laboratory busy. There therefore is a need for means for simplifying the quality control and determining the distribution of a colour and contrast intensive treatment composition on the individual kernel and between the kernels on the basis of a predetermined sample.

SUMMARY

The object was achieved by a device and a method, wherein the distribution of the colour and contrast intensive treatment composition is detected statistically by means of optical colour measurement (example: yellow grain—red treatment composition) of a substrate sample, consisting of a plurality of closely packed (=not individual) kernels, coated with a colour and contrast intensive coating composition.

Instruments for recording a colour image of a seed sample are known from the prior art. An example would be the kernel counter iXeed Counter by Hoopmann, which is based on colour scanner technology and is a table top instrument which establishes the process of counting and establishing the 1000-kernel weight and establishes the further characterization of a sample on the basis of a colour image of a seed sample. To this end, the seed sample is distributed on a glass plate and a colour image is recorded by means of an integrated colour scanner. The colour image is stored in an analysis unit and evaluated (http://www.hoopman-equipment.nl/images1/pdf/20091104_IXEED_COUNTER.pdf).

The use of the colour image obtained by the iXeed Counter for establishing the treatment quality of the seed sample has not been described. It can be assumed that the image obtained with the aid of the scanner does not have a sufficiently high quality to enable an in-depth colour analysis.

The device according to the invention comprises a portable video unit for recording a colour image of a substrate sample consisting of a plurality of closely packed kernels, connected to an image analysis unit in which a computer program for colour distribution analysis of the colour image recording is installed. According to the invention, the video unit comprises a colour video camera and illumination means, which are attached to a housing which is opaquely sealed around the video camera and has a recording window, wherein the video camera is directed at the recording window of the housing.

The housing forms an image recording chamber, which is only illuminated by the illumination means for recording the image. The housing can be round or polygonal, preferably polygonal.

The lens of the video camera is preferably perpendicular to and directed at the substrate surface.

For the colour recording, the video unit is positioned over the surface of the kernel-type substrate (e.g. in an open container full of kernel-type substrates).

The usual distance between lens and substrate surface is usually from 80 to 150 mm, preferably approximately 100 mm and the illumination means illuminate an area from preferably 40×40 mm to 150×150 mm, preferably 40×40 mm to 100×100 mm, particularly preferably approximately 75×45 mm.

The device according to the invention does not require the seeds to be examined to be separated into individual kernels, but rather measures the substrate sample in its entirety. As a result, particular preparation of the seed sample to be examined is avoided.

DETAILED DESCRIPTION OF A PREFERRED EMBODIMENT

In a special embodiment of the device, the substrate sample is introduced into a dimensioned bowl, which is then attached in a bowl-holding element as a further element of the video unit with a predeterminable distance from the video camera. The housing is usually positioned on the bowl-holding element. This guarantees that the prescribed distance between video camera and substrate is maintained. In this embodiment, the image recording chamber is also particularly well isolated from external light sources. For quality control of the coating quality in the case of grain such as wheat, use is typically made, without being restricted thereto, of a commercially available bowl with dimensions of 76×46 mm, in which, depending on size, there are between 100 and 300 kernels.

The video unit is designed as a mobile unit and can, with the aid of the housing, also be placed directly on any seed sample (e.g. in the seed bag).

A colour and contrast sensitive camera is used as colour video camera. A single-board USB colour video camera, which is as compact as possible, is preferably integrated into the video unit. For the purposes of optimum integration, preference is for a video camera without lens holder, which is integrated with a lens mount and a suitable lens into the video unit in a space saving fashion. By way of example, the single-board USB camera uEye UI-1248LE-C by IDS GmbH with a plastic lens mount for holding an M12 lens of the type B5M8430N by Lensation is particularly suitable. The lens mount preferably renders possible focussing at a short distance.

The illumination means preferably comprise one or more light-emitting diodes, in particular LED boards, as light sources.

In a preferred embodiment, the illumination means have a main printed circuit board connected to one or more diode boards for connecting light-emitting diodes.

Figure 6:
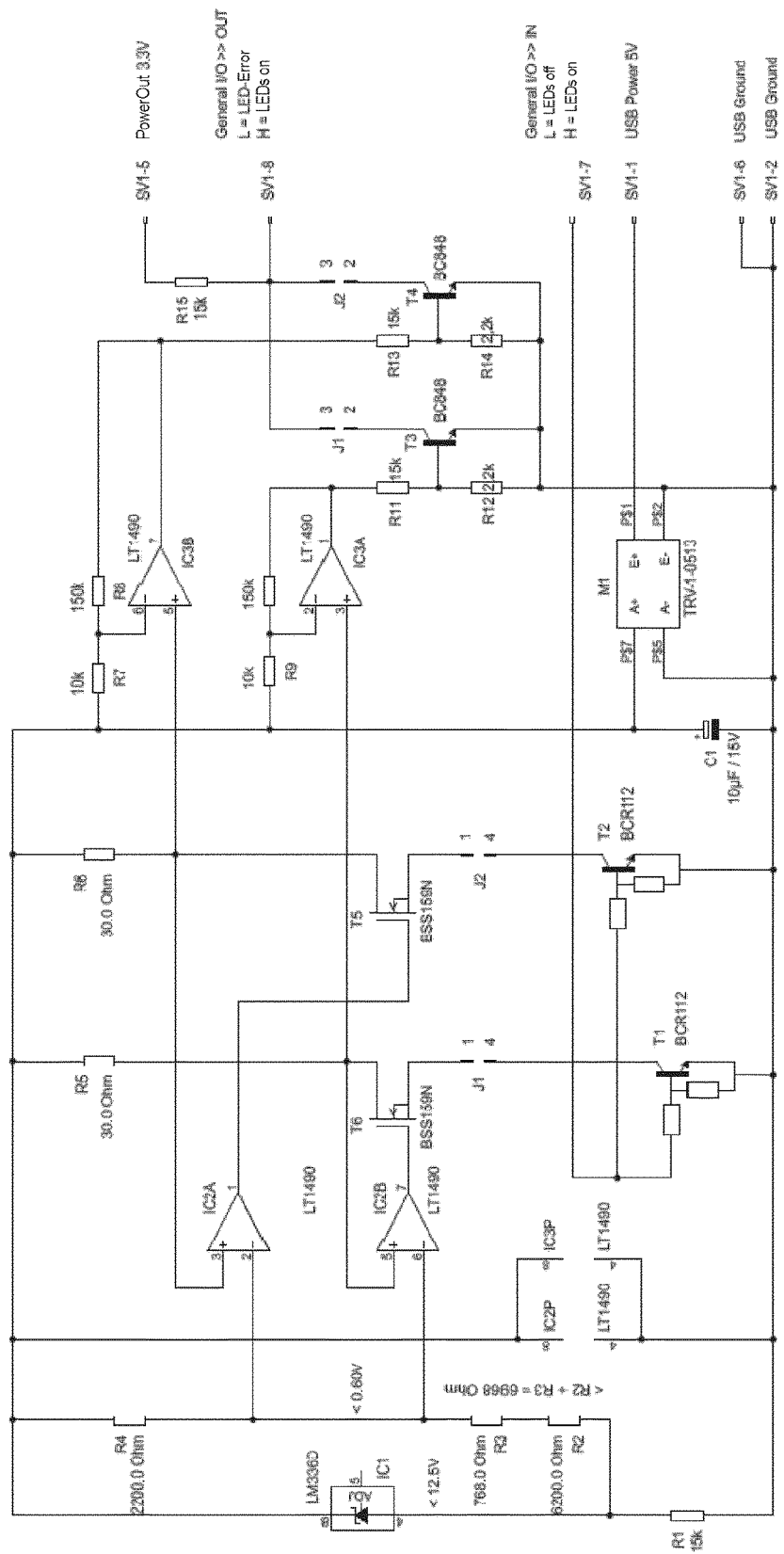

In the main printed circuit board, a contact strip serves for the connection to the colour video camera; it is simultaneously also used as a power supply for the diode boards and the connected light-emitting diodes. Available USB-IO inputs/outputs on the camera are used in conjunction with the board circuit for software-based switching on and off of the light-emitting diodes. The camera itself is usually screwed onto the main printed circuit board. FIG. 6 shows the circuit diagram of the main printed circuit board and the list of components thereof.

The diode boards are, in the design conventional in the prior art, provided for usually respectively holding two light-emitting diodes. By way of example, hole matrix boards of the type "Laborkarte RP2 Phenolhartpapier", manufactured by Rademacher, served as base material. Processing took place by sawing into the desired dimensions, soldering of respectively two light-emitting diodes and connection cables, and sealing using insulating varnish.

Luminous white light-emitting diodes with a luminous intensity of 5000 to 30 000 mcd are usually used as light source, such as, for example, light-emitting diodes by Nichia, Type NSPW310DS, luminous intensity $I_v$ 6800 mcd. Respectively two diodes are typically soldered in series on each diode board; the overall current is restricted to at most 2×20 mA by the circuit on the main printed circuit board.

For the purposes of an optimum illumination of the substrate, the light sources are preferably assembled below the video camera and laterally within the housing.

In order to minimize reflections on the substrate surface, the substrate surface is preferably only illuminated indirectly. To this end, the device according to the invention has a reflecting surface and one or more light sources.

In a preferred embodiment of the device, the reflecting surface consists of, from the interior of the image recording chamber, a concave matte white coated reflector, with a central bore for the lens of the camera and preferably with lateral bores for the illumination means.

The reflector is usually manufactured from a thin metal sheet and has the shape of a semi-cylindrical dome, wherein the interior of the dome is coated in a matte white fashion. Alternatively, the reflector is hemispherical or has a shape of the tunnel. A spherical dome-shaped reflector is preferred. The arching of the reflector is typically 120 to 200°, preferably 120 to 180, particularly preferably 180°.

The reflector usually has two to ten, preferably four to eight, preferably four, lateral bores for the same number of light-emitting diodes, preferably uniformly distributed on the circumference of the spherical dome or on the polygonal cross section of the semi-cylinder and level with the substrate surface. In the case of four light-emitting diodes, the USB connection with the control unit suffices for the power supply. The lines of the diodes are typically insulated up to the diode board using a shrink tube in order to avoid short-circuits by touching the metal reflector.

A barium sulphate coating formulation (e.g. supplied by Sphere Optics as spray-on suspension) as matte white coating is usually coated onto the interior of the dome as a reflecting surface of the reflector. This highly reflective coating guarantees a matte and uniform illumination of the seed samples to be examined.

In order to minimize reflections on the substrate surface further, the side of the light sources lying opposite to the substrate (underside) is preferably coated in a light-absorbing fashion, e.g. varnished with a light-absorbing layer, which simultaneously serves as eye protection for the user.

In order to prevent dirtying of the video camera optical system, there usually is a transparent plate, usually an acrylic glass plate, between the reflector and lens, from which, when necessary, dust can carefully be removed from the outside using pressurized air (<0.1 bar).

As an alternative to the reflector-based illumination means according to the invention, use can also be made of a light tunnel such as, e.g., an Xled-TU light tunnel by Planistar Licht GmbH, although this is afflicted with the disadvantage that such a light tunnel requires an additional external power supply.

The image analysis unit is usually a computer on which the software for image analysis is installed. The computer is usually connected to the video unit via a USB cable.

It was determined that reflector-based illumination means with four light-emitting diodes in one illumination chamber supply an illumination quality which enables the colour analysis of a colour image recorded in the illumination chamber. The USB connection to the computer suffices for the power supply of this video unit. This provides a simple completely portable device.

The analysis unit can record and store already recorded and stored image files and also direct images of substrate samples from the connected video unit.

Further subject-matter of the present invention relates to an optical method for establishing the distribution of colour and contrast intensive coating composition on a kernel-type substrate, in which a video unit is used to record a colour image of a substrate sample consisting of a plurality of closely packed kernels and the colour distribution on individual kernels is analysed by means of software for image analysis of the colour image.

The method according to the invention comprises the following steps:

1. recording a colour image of a coated multi-kernel substrate sample by means of the video unit,
2. transmitting the image recording to the image analysis unit,
3. entering substrate and coating composition colour F on an entry area of the image analysis unit. This coating composition colour F can either be entered manually into the image analysis unit or be extracted from the coating composition data module of the image analysis unit by selecting a coating composition on the entry area.
4. performing a spatially defined extraction of the colour information from the image with the aid of a computer program by comparing the colour of a point in the image recording to a reference value from the group comprising coating composition colour F, reference colour G of the substrate and/or the white balance with the aid of the software,
5. identifying blobs on individual kernels of the kernel substrate from the comparison of 4), and statistically evaluating the number of blobs and area covered by blobs on individual kernels of the kernel substrate with the aid of the computer program and 6. outputting the blob distribution on the individual kernels, also referred to as "patchiness", on the basis of the number of blobs from an output area of the image analysis unit.

In a preferred embodiment of the method according to the invention, the following step is moreover also carried out:

7. statistical evaluation of the area of the recognized blobs with the aid of the computer program and outputting the kernel-to-kernel distribution, also referred to as "evenness", on the basis of the area covered by blobs.

In a preferred embodiment of the method according to the invention, during step 4, the image is subdivided into regions by means of a grid with a predefined grid mesh. The area of a region is set by the grid mesh for the kernel-type substrate to be examined. The grid mesh is usually 20 to 80% of a kernel, preferably 40 to 60%, particularly preferably 50% of a kernel. The optimum grid mesh for the kernel-type substrate to be examined can either be entered into the image analysis unit or can be extracted from a substrate data module of the image analysis unit by selecting a substrate on the entry area. The grid mesh is typically from 1 mm×1 mm to 20 mm×20 mm for seeds.

In step 4, the colour information is usually extracted in the red-green-blue model (RGB colour model) of the colour space. To this end, the red-green-blue information is preferably compared to the white balance.

In step 5, the extracted red-green-blue information is preferably converted into HSI information (hue, saturation, intensity colour model), in which the hue is characterized as a colour angle H on a colour circle. This conversion is brought about according to an already known method (see e.g. http://de.wikipedia.org/wiki/HSI-Farbmodell). In step 5, it is preferable for only those points whose colour angle H is situated between two thresholds and corresponds to the coating composition colour F to be selected. From this selection, contour and area of the blobs are identified on the basis of the position of the selected points (Blob detection, see http://en.wikipedia.org/wiki/Blob_detection). The number of blobs and the area thereof are calculated.

An HSI colour histogram is optionally established for each region.

In the statistical evaluation according to step 5, a small number of blobs per region together with a large area covered by blobs per region corresponds to a uniform distribution of the coating composition (good patchiness). However, a large number of blobs with a large area covered by blobs indicates a strongly but poorly distributed coating of the substrate (bad/high patchiness).

Figure 8:
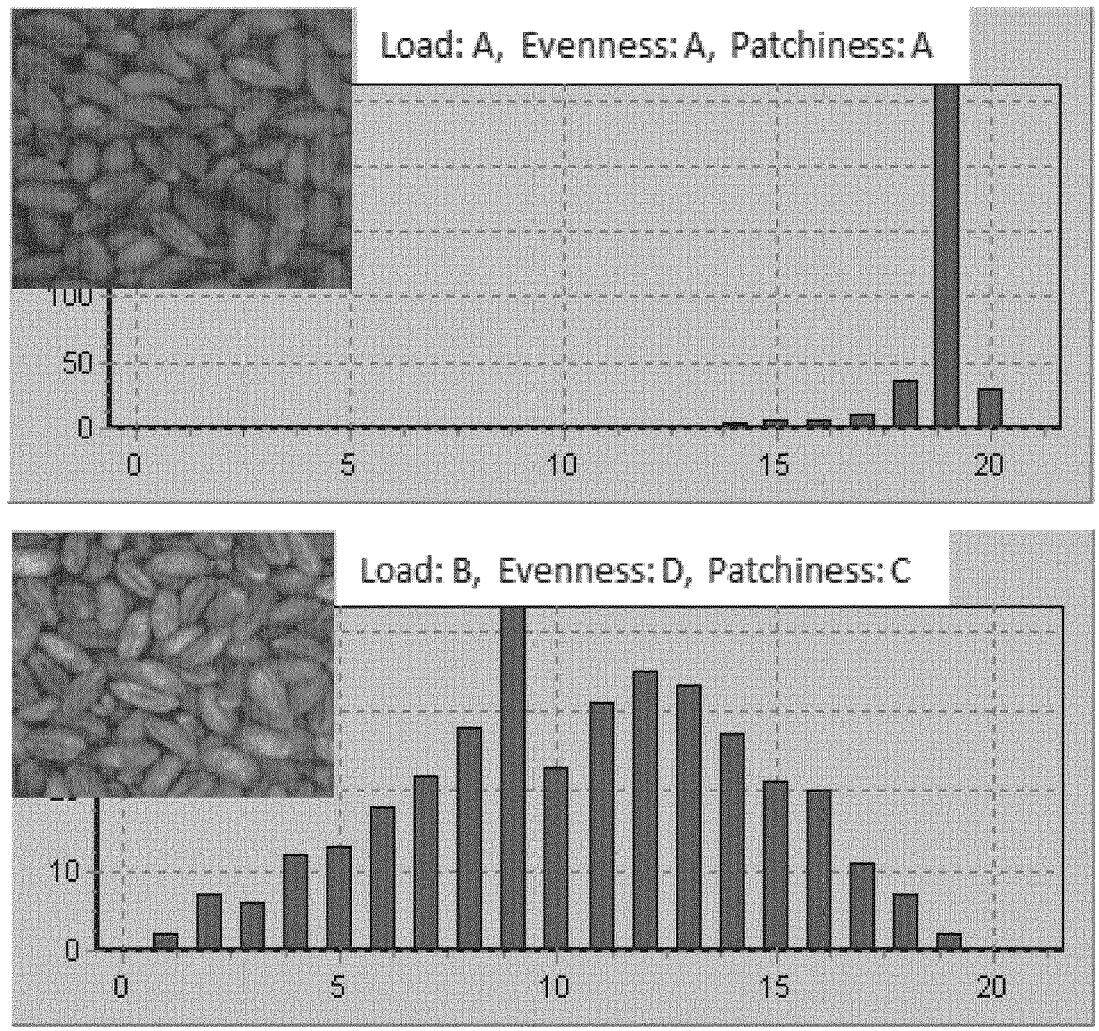

In step 7, a new histogram for the complete image is created from all areas covered by blobs per region. To this end, the precisely established area values are usually rounded into 5% interval regions. FIG. 8 shows such a histogram of the % area covered by blobs with respect to the area of the region. The total area of the histogram indicates the coated amount (=load). If the area of the histogram is large, the load is good; a low area of the histogram indicates a bad coating (bad load=hardly coated amount). Strong scattering in the histogram indicates a poor evenness of the coating over the whole sample.

Using the method according to the invention, it is possible to generate statistics in respect of, firstly, the kernel-to-kernel (overall) distribution and, secondly, the distribution on the individual kernels for a substrate sample by non-invasive means and with a minimum amount of effort. The two statistical parameters are referred to as "evenness" and "patchiness".

The percentage of overall cover, including the average value, of the kernel surface as a result of the treatment composition is also preferably established and specified as "load" and "ave". The quality values established using the method according to the invention enable a detailed reproducible evaluation of the quality of the coating procedure.

The device according to the invention can be applied, in particular, for quality assurance of seed treatment procedures using plant protection formulations, especially in the case of grain. The quality assurance is achieved by a colour analysis by way of optical detection. For the purposes of a reliable statement, a sufficient colour and intensity contrast of the formulation relative to the seed must be ensured. A highest possible degree of cover of the formulation is also advantageous. Measurements using the device and method according to the invention only take place after complete drying of the applied formulation, since the colour only then is stable and the instrument is not waterproof or protected against spray water.

A further application of the device according to the invention lies in the optical control of a seed sample in respect of further colour and contrast intensive staining, such as, for example, staining caused by fungi.

Thus, within the meaning of the present invention, coating composition is a coating material, treatment composition or other staining material, which, compared to the substrate, is colour and contrast intensive.

Coating composition with a small colour and intensity difference relative to the substrate under white light conditions can likewise be detected by optimizing the illumination, in particular the composition of the wavelength of the illumination light.

The operation of the image analysis unit is illustrated in an exemplary fashion in the following example, without being restricted to this.

FIGURES

Figure 1:
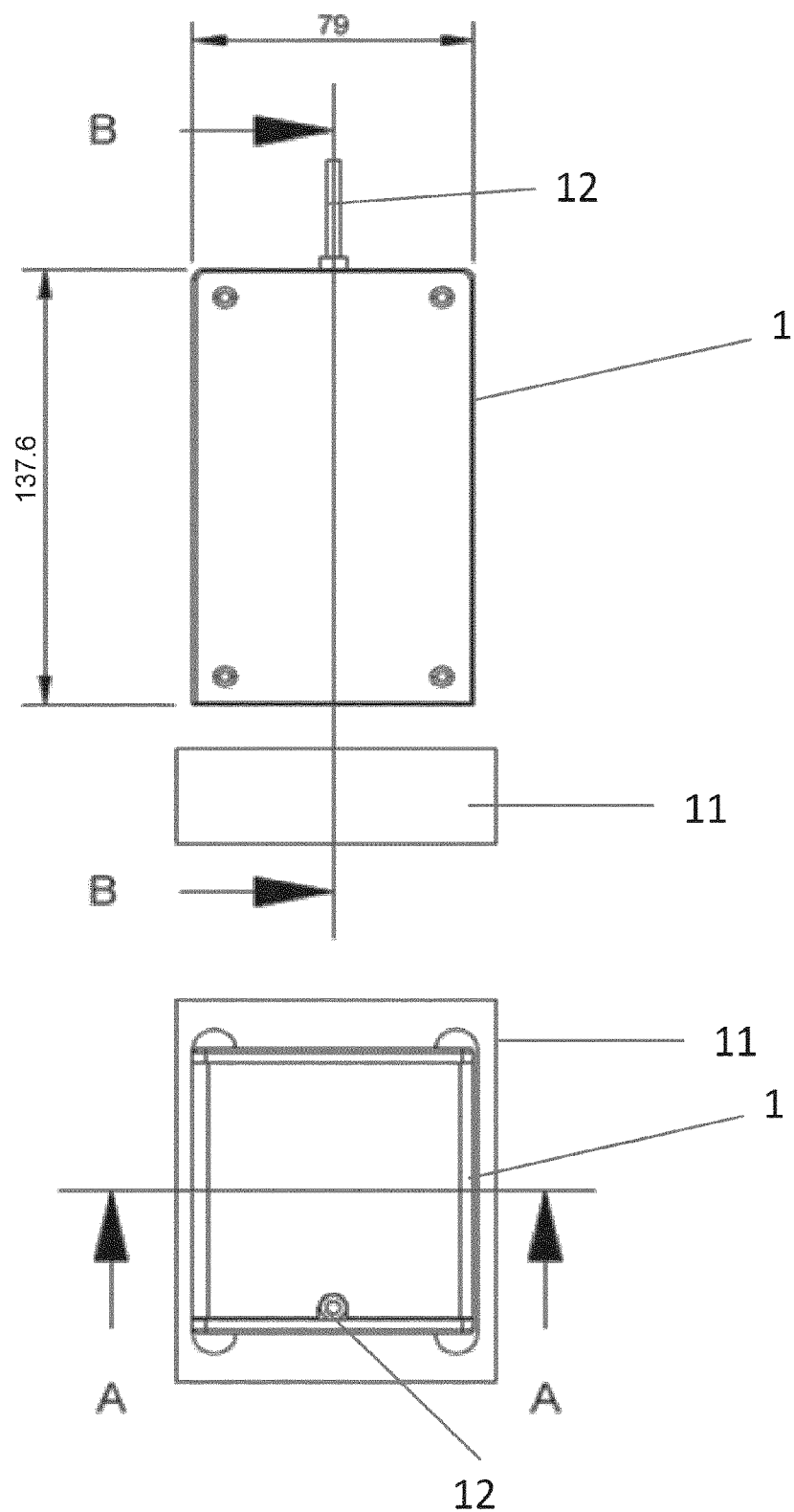
FIGS. 1-9 represents embodiments described herein.

FIG. 1 shows a schematic illustration of the video unit according to the invention (laterally and from the top)

Figure 2:
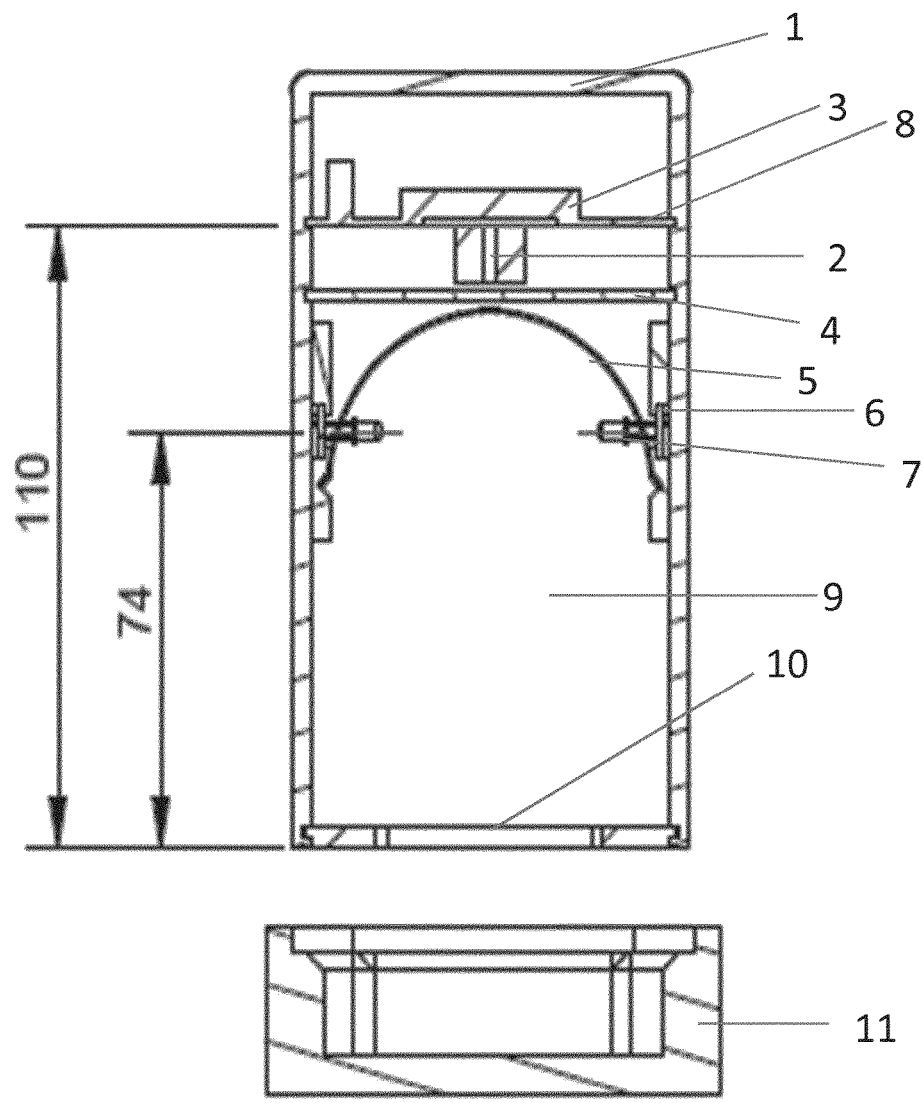

FIG. 2 shows the interior of the housing along the section A-A

Figure 3:
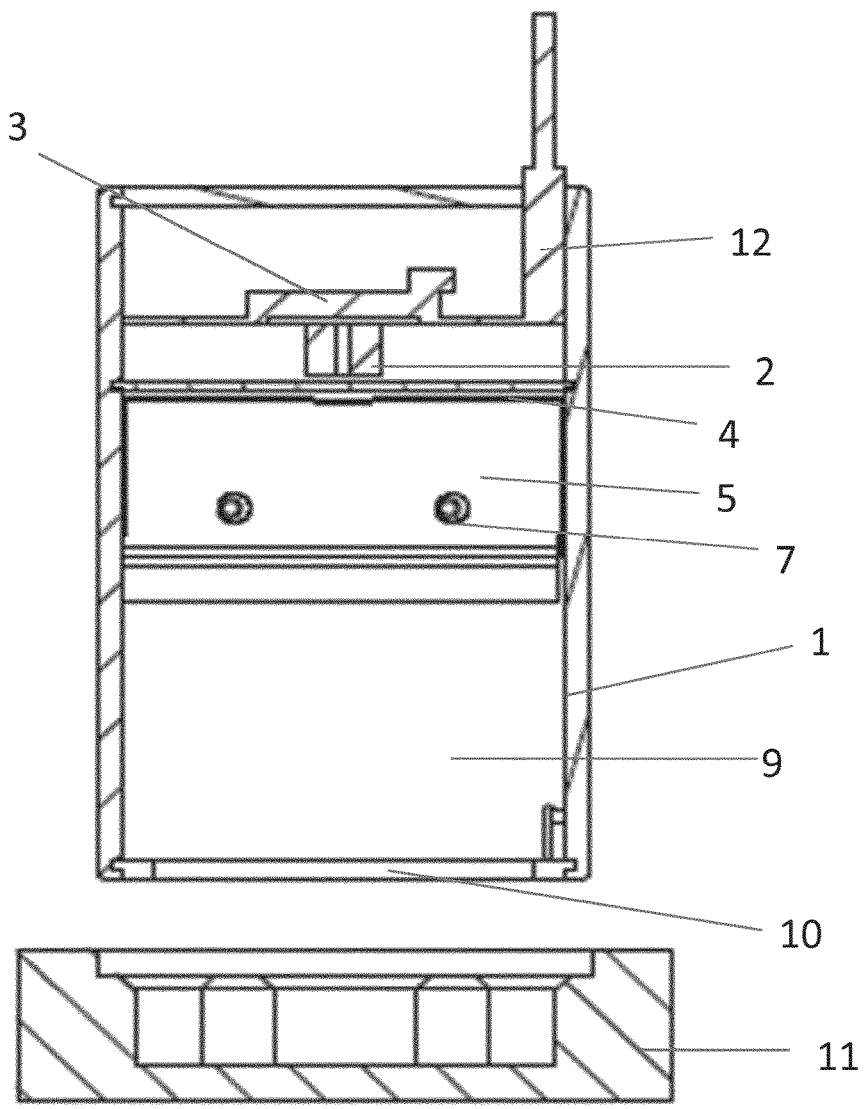
Figure 4A:
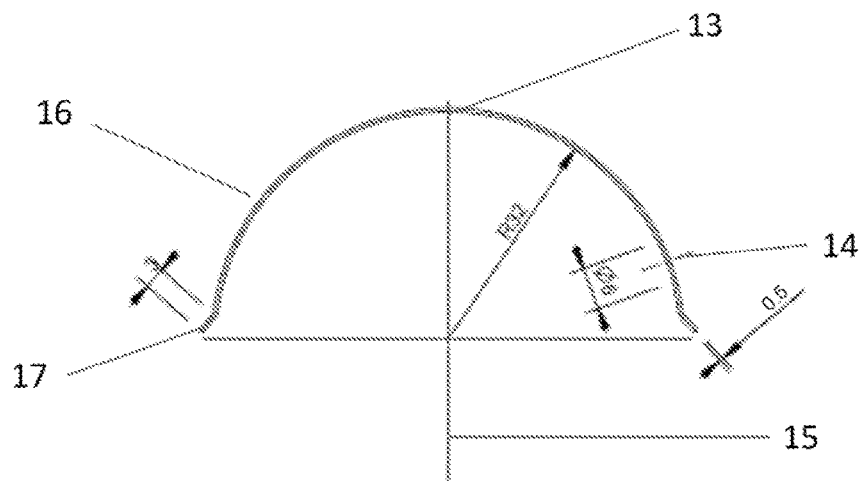
Figure 4B:
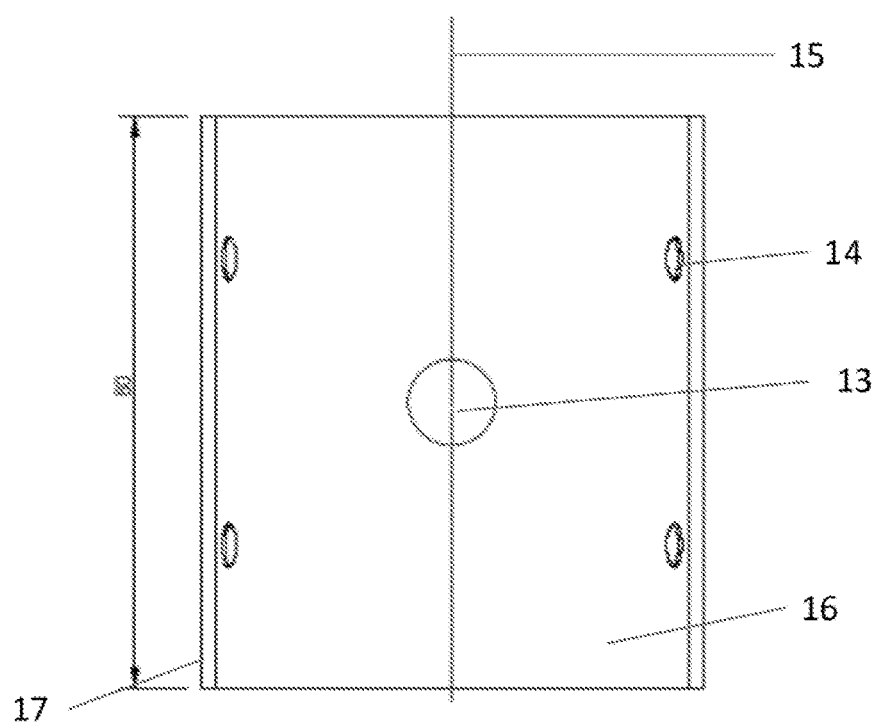
Figure 5:
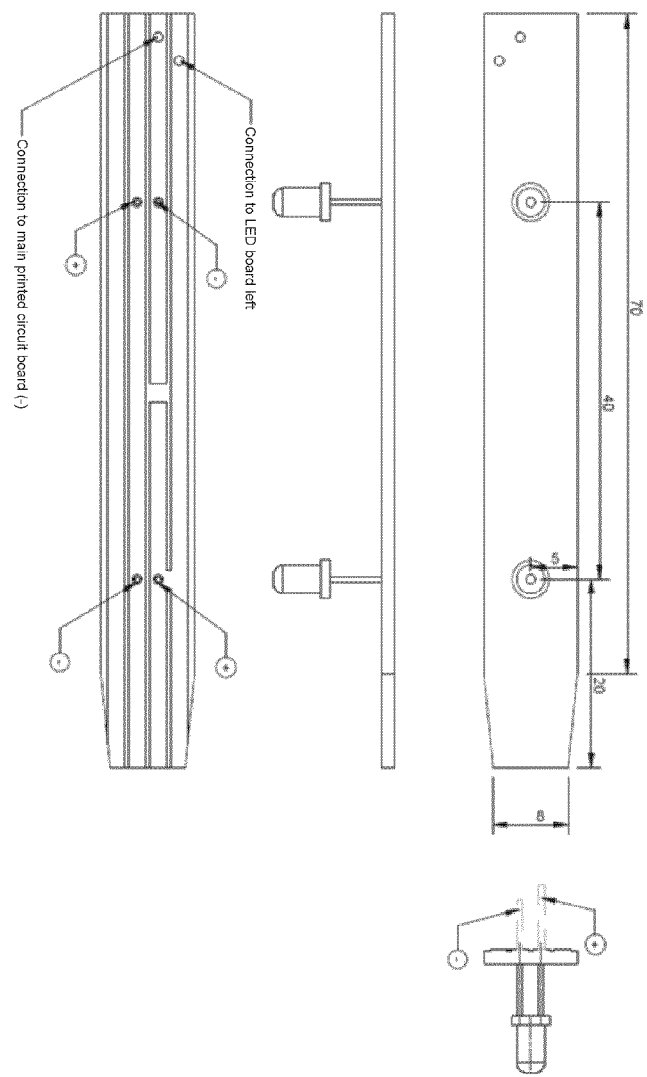
Figure 7:
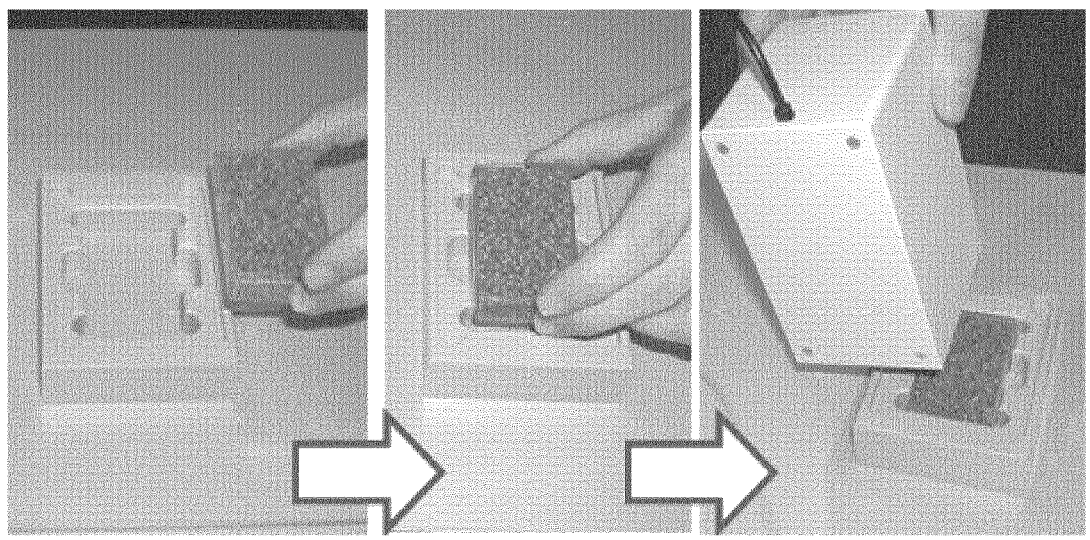
Figure 9:
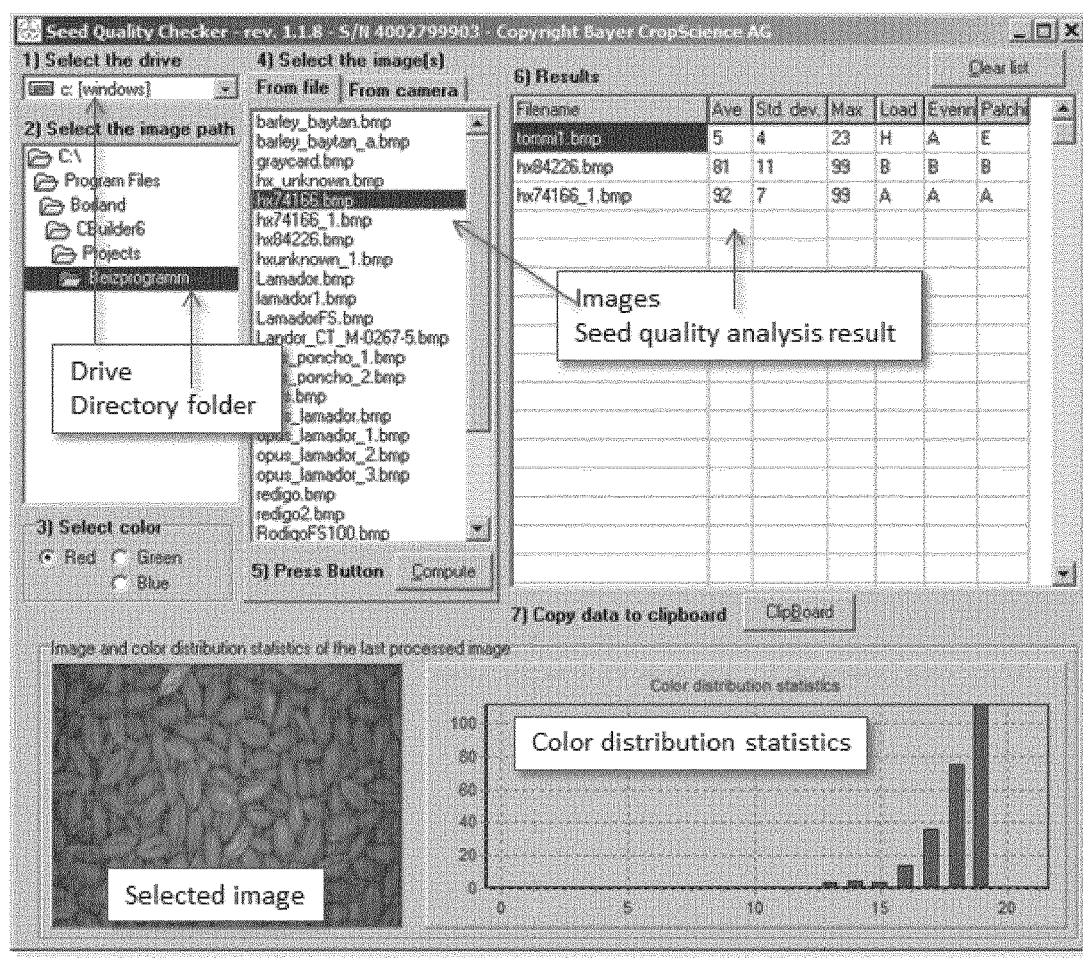

FIG. 3 shows the interior of the housing along the section B-B in the case of a cylindrical metal reflector FIGS. 4a and 4b show the design of the cylindrical reflector in cross section and from below FIG. 5 shows the design of the diode boards FIG. 6 shows the design of the main printed circuit board (circuit diagram) and the components thereof FIG. 7 shows the image recording of a seed sample in a Petri dish, which is placed in the bowl-holding element of the video unit FIG. 8 shows a colour histogram "colour distribution statistics", illustrated by way of a graph FIG. 9 shows the output main form

LIST OF REFERENCE SIGNS

1. Housing of the video unit
2. Camera body and optical unit
3. Plate (or main printed circuit board?)
4. Camera protection plate
5. Reflector
6. Diode board 7. Light-emitting diode
8. Main printed circuit board
9. Illumination chamber
10. Image recording window
11. Bowl-holding element
12. USB cable
13. Camera bore
14. Diode bore
15. Reflector axis
16. Reflector curvature
17. Reflector connection

EXAMPLE

In the following example, the image analysis unit serves both to control the video unit and to carry out the image analysis of the recorded colour image.

The sequence of the individual actions is characterized by numbering from 1) to 7); this simplifies the operation (see image).

In the following text, the individual steps are explained in detail.

1) "Select the drive": select the drive to which the recorded images from the video unit are copied; the directory is set in the next step.
2) "Select the image path": select the directory into which the images from the video unit are copied.
3) "Select seed": select the seed. In the following example, wheat was selected.
4) "Select colour": select the coating composition colour F of the treatment composition, the standard is red.
5) "Select the image(s)": select the seed images to be checked. Two options are available for selection:
   a. "From file": it is possible to select a plurality of already recorded images. The first image is marked by mouse click, every further image by mouse click while at the same time pressing the control key ("Strg" or "Ctrl").
   b. "From camera": in this case, the image of a seed sample can be recorded and stored by means of the connected video unit; this function will be described in detail in the next section.
6) "Press button": the key "compute" starts the analysis of the previously marked images and transmits the results into the table. This point is dispensed with when recording images with the video unit (see next section).
7) "Results": in this list, the results are displayed in table form. A detailed description follows in the next but one section. The list can be deleted at any time by means of the key "clear list".
8) "Copy data to clipboard": copies the table to the clipboard. The data can subsequently be processed further.

Recording Images of Seed Samples

The image recording and evaluation of a new seed sample can be brought about in two different ways using the video unit:
   a. placing the video unit on the planar seed surface of a seed sample,
   b. filling the seed sample into a Petri dish, wherein the dish is filled up to the edge and then inserted into the bowl-holding element of the video unit. As a last step, the image recording chamber is placed onto the bowl-holding element (FIG. 7).

An image of the seed sample is subsequently recorded in both cases. To this end, the tab "From camera" (point 4) is selected in the program:

After entering a file name, a new image of the seed sample is recorded by pressing "new frame"; the image is stored in the directory selected in point 2). There is no need to enter the file extension; the software stores all images in the uncompressed bitmap format.

Finally, the image is analysed and evaluated according to the method according to the invention and the result of the analysis is transferred to the table.

Image Analysis:

a) Spatially defined extraction of the colour information from the image as red-green-blue information. For the purposes of the spatially defined extraction of the colour information, the image of the wheat sample was subdivided into regions by means of a grid having a grid mesh with the dimensions of 4 mm×4 mm (50% of the seed dimensions).
b) Then red-green-blue information was converted into HSI information; a colour histogram was established for each region. Those points were selected whose colour angle H is greater than the angle of the coating composition colour F. Contours of the blobs were identified for each region from this selection on the basis of the position of the selected points and the area of the blobs was calculated. The number of blobs was also established. These values are used for evaluating the patchiness.

For the purposes of establishing the treatment level/evenness, the areas covered by blobs per region were summed and a new histogram was created for the complete image. To this end, the precisely calculated area values were rounded into 5% interval regions.

Output of the Analysis:

The first column of the result table always contains the name of the image file, the further six columns contain the results of the analysis. The following parameters are usually established from the analysis:

"Ave": mean degree of cover of the seed by the treatment composition, specified as %-value of the visible seed area.

"Std. Dev." (=Standard deviation): standard deviation of the mean degree of cover (Ave), specified as %-value of the visible seed area.

"Max" (=max load): maximum treatment level of individual seed kernels, specified as %-value of the visible seed area.

"Load": treatment level, established by colour analysis of the sample. Specified as a scale in text form from "A" for very high to "H" for very poor treatment level.

"Evenness": measure for the kernel-to-kernel distribution of the treatment. Specified as a scale in text form from "A" for very even to "H" for extremely uneven treatment.

"Patchiness": measure for the distribution of the treatment composition of individual kernels ("spots"). Specified as a scale in text form from "A" for very homogeneous to "H" for extremely patchy treatment (individual spots).

The statistical distribution of the treatment composition is illustrated by means of a graph in the diagram "colour distribution statistics" (see FIG. 8). FIG. 8 shows, in such a histogram, the % area covered by blobs to the area of the region. The overall area of the histogram indicates the coated amount (=treatment level). If the histogram area is large, the treatment level is good; a small histogram area indicates a poor coating (poor treatment level=poorly coated amount). Strong scattering of the histogram indicates a poor evenness of the coating over the whole sample.

FIG. 9 shows the output main form for outputting the relative quality values and graphical illustration.

The invention claimed is:

1. Optical method for establishing the distribution of a colour and contrast intensive coating composition on a kernel-type substrate, in which a video unit is used to record a colour image of a substrate sample consisting of a plurality of closely packed kernels and the colour distribution on individual kernels is analysed by means of a computer program for image analysis of the colour image, comprising:
   a. recording a colour image of a coated multi-kernel substrate sample by means of the video unit,
   b. transmitting the image recording to an image analysis unit,
   c. entering substrate and coating composition colour F on an entry area of the image analysis unit,
   d. performing a spatially defined extraction of the colour information from the image with the aid of the software by comparing a colour of a point in the image recording to a reference value from the group comprising coating composition colour F, reference colour G of the substrate and/or the white balance with the aid of the software, wherein, during d), the image is subdivided into regions by means of a grid with a predefined grid mesh
   e. identifying blobs on individual kernels of the kernel substrate from the comparison of d), and statistically evaluating the number of blobs and area covered by blobs on individual kernels of the kernel substrate with the aid of the software and
   f. outputting the blob distribution on the individual kernels, also referred to as "patchiness", on the basis of the number of blobs,
   wherein the colour and contrast intensive coating composition comprises a treatment composition.

2. Method according to claim 1, furthermore comprising a statistical evaluation of the area of the recognized blobs with the aid of the computer program and outputting the kernel-to-kernel distribution, also referred to as "evenness", on the basis of the area covered by blobs.

3. Method according to claim 1, wherein the grid mesh is 20 to 80% of a kernel.

4. Method according to claim 1, wherein only those points whose colour angle H is situated between two thresholds and corresponds to the coating composition colour F are selected in d).

5. Method according to claim 4, wherein contour and area of the blobs are calculated on the basis of the position of the selected points.

6. Method according to claim 1 for optical control of a seed sample in respect of colour and contrast intensive staining or coating quality using a colour and contrast intensive coating composition.

* * * * *